United States Patent [19]

Frisch

[11] Patent Number: 5,226,945
[45] Date of Patent: Jul. 13, 1993

[54] AQUEOUS HERBICIDAL DISPERSION CONCENTRATE CONTAINING LINURON AND MONOLINURON AS ACTIVE SUBSTANCES

[75] Inventor: Gerhard Frisch, Wehrheim, Fed. Rep. of Germany

[73] Assignee: Hoechst Aktiengesellschaft, Frankfurt am Main, Fed. Rep. of Germany

[21] Appl. No.: 778,393

[22] Filed: Oct. 16, 1991

[30] Foreign Application Priority Data

Oct. 18, 1990 [DE] Fed. Rep. of Germany ....... 4033035

[51] Int. Cl.$^5$ ............................................. A01N 47/30
[52] U.S. Cl. ................................. 504/148; 71/DIG. 1
[58] Field of Search ............................ 71/120, DIG. 1

[56] References Cited

U.S. PATENT DOCUMENTS

| 3,888,828 | 6/1975 | Grossmann | 71/93 |
| 4,594,096 | 6/1986 | Albrecht et al. | 71/93 |
| 4,804,399 | 2/1989 | Albrecht et al. | 71/93 |

FOREIGN PATENT DOCUMENTS

| 562459 | 5/1984 | Australia. |
| 0110174 | 6/1984 | European Pat. Off. . |
| 0297305 | 1/1989 | European Pat. Off. . |
| 2132405 | 1/1973 | Fed. Rep. of Germany . |
| 2144415 | 2/1973 | France . |

OTHER PUBLICATIONS

*The Agrochemicals Handbook,* "Linuron" pA248: editors D. Hartley and Hamish Kidd; Royal Society of Chemistry, England 1987.

*Primary Examiner*—Richard L. Raymond
*Assistant Examiner*—B. Bembenick
*Attorney, Agent, or Firm*—Curtis, Morris & Safford

[57] ABSTRACT

Aqueous herbicidal dispersion concentrate containing linuron and monolinuron as active substances Storage-stable, aqueous herbicidal dispersion concentrate containing (a) linuron and monolinuron as active substances and
(b) an alkali metal salt of a sulfosuccinic monoester as dispersant, prepared by reacting a polyglycol ether of a condensation product of a ($C_8$–$C_{12}$)-alkylphenol and formaldehyde with maleic anhydride and an alkali metal sulfite, the dispersion concentrate having a pH from 2.5 to 7.5.

14 Claims, No Drawings

AQUEOUS HERBICIDAL DISPERSION CONCENTRATE CONTAINING LINURON AND MONOLINURON AS ACTIVE SUBSTANCES

The present invention relates to an aqueous herbicidal dispersion concentrate containing linuron and monolinuron as active substances.

To date, it is known that the herbicides linuron [3-(3,4-dichlorophenyl)-1-methoxy-1-methylurea] and monolinuron [3-(4-chlorophenyl)-1-methoxy-1-methylurea] exist as mixed formulations in the form of wettable powders and formulations in the form of emulsion concentrates (commercial product Afalon S ®, manufactured by HOECHST AG).

However, expensive grinding and filtering plants are required in the preparation of wettable powder formulations, and also frequently expensive carriers. Wettable powders also have the disadvantage that they produce dust during handling. They can only be dosed with difficulty. The user can easily become contaminated by such formulations which produce dust, and suffer damage. Furthermore, spray mixtures prepared from wettable powders tend to be inhomogeneous; the active substance particles and solids particles settle relatively rapidly.

In particular, the emulsion concentrates of the two abovementioned active substances have the disadvantage that it is only possible to achieve a low active substance content of 90:90 g/l.

Since aqueous dispersions do not have the disadvantages of the wettable powders and, in principle, allow higher active substance contents because linuron and monolinuron are insoluble in water, and because they can also be prepared with a relatively low outlay in terms of equipment, attempts have been made to prepare aqueous dispersions of both active substances with a markedly higher active substance content than, for example, the emulsion concentrates; however, such attempts have failed to date, namely because of crystal growth owing to the relatively good solubility of the two active substances in water, because of grinding problems, etc.. Such attempts gave dispersions of low stability which showed substantial flocculation, sedimentation or even solidification. Even the use of coloring matter for preventing crystallization did not result in the desired aim of providing an aqueous dispersion of linuron with monolinuron which shows long-term stability (2 years at room temperature or 3 months at 50° C.), does not show crystal growth, which puts stability at risk, and which does not flocculate, sediment or even solidify.

Emulsifiable concentrates and wettable powders exist in the form of one-phase systems; in contrast, aqueous dispersion concentrates of solid active substances represent two-phase systems (solid/liquid), which, in general, are instable and their mixture tends to separate, this tendency increasing with increasing storage time and temperature. Practical requirements demand that dispersion concentrates must be storage-stable over two years; they must furthermore remain pourable. The solidification of dispersions and/or the formation of irreversible sediments must be excluded.

Even though there exist theoretical considerations as to the conditions for establishing stable suspensions, it is impossible to predict optimum formulation additives directly because of the large number of criteria to be taken into account. In practice, it is usually insufficient, for example, to investigate the suspension behavior of an individual production batch since minute changes in amounts of secondary components in the individual active substance batches can decisively impair the stability of the dispersions.

Optimum formulation of herbicidal ureas, for example linuron, using partially hydrolyzed polyvinyl acetates, as described in U.S. Pat. No. 4,071,617, has therefore proved to be impossible since viscous sediments which are not redispersible are formed when these formulation additives are used. If nonionic emulsifiers, vegetable gums and anionic surface-active agents, for example in accordance with U.S. Pat. No. 3,948,636 or British Patent Specification 148,010, are employed, the same effect becomes apparent.

EP 0,110,174 discloses liquid pesticidal compositions in the form of aqueous suspension concentrates which contain, besides the active substance, the following essential components:

(1) an alkali metal salt of a sulfosuccinic monoester, prepared by reacting a polyglycol ether of a condensation product of ($C_8$- to $C_{12}$)-alkylphenol and formaldehyde with maleic anhydride and an alkali metal sulfite,
(2) an alkali metal salt of a lignosulfonic acid and
(3) a swellable alkaline earth metal silicate, components (2) and (3) being present in the mixture in equal parts.

This European Patent specifically emphasizes the complete loss of the advantageous properties, i.e. in particular the storage stability and pourability, of the suspension concentrate when only one component of the three essential formulation ingredients sulfosuccinic monoester, salt of lignosulfonic acid and swellable alkaline earth metal silicate is absent, which has also been demonstrated by comparison tests. From amongst a large number of pesticides, linuron and monolinuron are, inter alia, generally mentioned as herbicidal active substances which can be employed. No mention is made in this publication of the essential importance of the pH of the suspension concentrate.

Surprisingly, it has now been found that storage-stable aqueous herbicidal dispersion concentrates having a considerably higher active substance content of linuron and monolinuron compared with the emulsion concentrates known to date can be obtained when the dispersing agent used is an alkali metal salt of a sulfosuccinic monoester, prepared by reacting a polyglycol ether of a condensation product of a ($C_8$- to $C_{12}$)-alkylphenol and formaldehyde with maleic anhydride and an alkali metal sulfite, and the pH of the concentrate is adjusted to 2.5, preferably 3.0, to 7.5.

The present invention therefore relates to an aqueous herbicidal dispersion concentrate containing a) linuron and monolinuron as active substances, and
b) an alkali metal salt of a sulfosuccinic monoester as dispersant, prepared by reacting a polyglycol ether of a condensation product of a ($C_8$–$C_{12}$)-alkylphenol and formaldehyde with maleic anhydride and an alkali metal sulfite, having a pH from 2.5, preferably 3.0, to 7.5.

The dispersion concentrate preferably furthermore contains a cosurfactant selected from the group comprising lignosulfonates, alkali metal salts of a sulfonic acid of an aromatic condensation product, and alkali metal salts of a sulfonic acid of a polymeric aromatic substance, this cosurfactant mainly acting as an improver of the dispersing and grinding properties.

As shown by comparison tests below, both the abovementioned specific dispersant and the specific pH range are critical.

The alkali metal salt of a sulfosuccinic monoester, in particular the sodium salt, which is employed in the dispersion concentrate according to the invention can be prepared analogously to German Patent Specification 2,132,405, where, in particular, monooctylphenols or mononoylphenols are employed and where the molar ratio of alkylphenol to formaldehyde varies within the range from 2:1 to 10:9. The polyglycol ether of this condensation product of alkylphenol and formaldehyde preferably contains 2 to 8 mol of alkylene oxide units, in particular ethylene oxide units, per mol of alkylphenol. The alkali metal sulfite used is preferably sodium sulfite.

A sulfosuccinic monoester prepared from 3 mol of nonylphenol, 18 mol of ethylene oxide, 2 mol of formaldehyde, 3 mol of sodium sulfite and 3 mol of maleic anhydride is preferred; it can be employed in the form of a dry powder or in the form of an aqueous solution (in general 35% strength).

The dispersion concentrate according to the invention contains the alkali metal salt of the sulfosuccinic monoester in an amount of from approximately 0.1 to approximately 20% by weight, preferably 2–16% by weight.

The dispersion concentrate can contain linuron and monolinuron each in an amount of from approximately 8 to approximately 35, preferably 7 to 23% by weight; accordingly, the active substance content which is possible is considerably higher than that of the known emulsion concentrates.

The ratio by weight of the active substances linuron:monolinuron is approximately 10:1 to 1:10, in particular approximately 1:1.

As mentioned above, the dispersion concentrate according to the invention preferably contains a specific cosurfactant; such surface-active compounds are commercially available, mention being made of the products mentioned in the notes to Tables I and II below. If at all, the dispersion concentrate according to the invention contains the cosurfactant in an amount of from 0.1 to 8% by weight, preferably 1 to 5% by weight.

The pH of the dispersion concentrate is essential for the stability of the latter. It is advantageously below approximately 7.5 and above 2.5, better approximately 3. The pH is preferably 3.5 to 7.0. If the abovementioned broad pH range is not adhered to, the dispersion concentrate tends to become instable within a short time.

The pH can be adjusted using buffer systems, advantageously citric acid including the ammonium and alkaline earth metal salts thereof, or dihydrogen phosphates, for example $KH_2PO_4$.

The dispersion concentrates according to the invention can additionally contain conventional formulation auxiliaries such as freezing-point depressants for increasing stability to frost, thickeners for improving the viscosity, and preservatives and/or defoamers.

Examples of freezing-point depressants are, inter alia, ethylene glycol, propylene glycol, glycerol, urea and the like.

Viscosity improvers which can be employed are customary inorganic or organic thickeners; examples of the latter are those based on polysaccharides (for example the commercial products Rhodopol 23 ® supplied by Rhone Poulenc and Kelzan ® supplied by Kelco Corp.), based on polyvinyl alcohols (commercial product Mowiol ® supplied by HOECHST AG), or based on methylcellulose (for example the commercial product Tylose ® supplied by HOECHST AG).

Examples of preservatives are benzoic acid, sorbic acid, formaldehyde and traces of fungicidal active substances (for example the commercial products Bronidox L ® supplied by Henkel KGaA, Kobate C ® supplied by Rhone Poulenc, Mergal KM 200 ® supplied by Riedel-de Haen).

Finally, examples of defoamers are those based on silicone (commercial products Silcolapse ® supplied by Rhone Poulenc, and the antifoam range supplied by Wacker Chemie GmbH, for example the defoamer SE 2).

To prepare the dispersion concentrates according to the invention, the components are stirred with water, then, if appropriate, the resulting coarse suspension is comminuted by grinding on a corundum mill or a toothed-disk mill to a fineness of approximately 200 microns, and the product is subsequently ground in ball mills or sand mills until the particles of the dispersion exist in particle sizes from 0.1 to 10 microns, preferably below 5 microns. The particle sizes are determined by means of a disk centrifuge or a Coulter counter.

The dispersion concentrate according to the invention is applied in a simple manner by diluting the dispersion concentrates with the desired amount of water, stirring the mixture briefly and applying it to the plant. Compared with spray mixtures prepared from wettable powders or emulsifiable concentrates, the spray mixtures obtained from the dispersion concentrates according to the invention are distinguished, in particular, by a uniform distribution of the active substances which is retained even after a standing period of 24 hours. In contrast, suspensions of wettable powders undergo rapid separation; often, half of the active substance has settled after a standing time of half an hour. In contrast, emulsions have the disadvantage that they can only be prepared with a low content of the active substances linuron and monolinuron, as has already been mentioned above.

The examples which follow are intended to illustrate the invention in greater detail.

EXAMPLES 1 to 20

Aqueous suspension concentrates containing linuron and monolinuron as active substances were prepared from the components mentioned in each case in Table I below by grinding the constituents in a ball mill using glass spheres of diameter 2 mm.

The dispersions were ground to such a fineness that 90% by weight of the suspended particles had a diameter of less than 5 microns and 30 to 40% by weight of the particles a diameter of less than 1 micron, the particle sizes being measured by means of a disk centrifuge.

At a storage time of 3 months at 50° C., the compositions according to the invention mentioned in Table I proved to be stable and satisfactory as regards their application properties.

COMPARISON EXAMPLES 1 to 7

In contrast, the compositions mentioned in Table II show flocculation and extensive sedimentation, in some cases even solidification. This is caused by the fact that they did not contain the dispersant alkali metal salt of a sulfosuccinic monoester according to the invention and/or had a pH above 7.5 (upper limit according to the invention).

TABLE I

| Examples | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Linuron | 8.7 | 17.3 | 17.3 | 17.3 | 17.3 | 17.3 | 17.3 | 17.3 | 17.3 | 17.3 | 17.3 | 17.3 | 17.3 | 17.3 | 17.3 | 17.3 | 17.3 |
| Monolinuron | 8.7 | 17.3 | 17.3 | 17.3 | 17.3 | 17.3 | 17.3 | 17.3 | 17.3 | 17.3 | 17.3 | 17.3 | 17.3 | 17.3 | 17.3 | 17.3 | 17.3 |
| Defoamer[1] |  | 2.0 | 2.0 | 2.0 | 2.0 | 2.0 | 2.0 | 2.0 | 2.0 | 2.0 | 2.0 | 2.0 |  |  |  |  |  |
| Defoamer[2] | 1.0 |  |  |  |  |  |  |  |  |  |  |  | 1.0 | 1.0 | 1.0 | 1.0 | 1.5 |
| Glycerol |  |  |  |  |  |  |  |  |  |  |  |  | 8.0 |  |  |  | 8.0 |
| Propylene glycol | 8.0 | 8.0 | 8.0 | 8.0 | 8.0 | 8.0 | 8.0 | 8.0 | 8.0 | 8.0 | 8.0 | 8.0 |  | 8.0 |  |  |  |
| Urea |  |  |  |  |  |  |  |  |  |  |  |  |  |  | 6.0 | 6.0 |  |
| Dispersant[3] | 16.0 | 4.0 | 4.0 | 4.0 | 4.0 | 5.0 | 4.0 | 4.0 | 5.0 | 6.0 | 4.0 | 4.0 | 5.0 | 4.0 | 4.0 | 4.0 | 4.0 |
| Cosurfactant[4] |  |  | 2.0 |  |  |  |  |  |  |  |  |  |  |  |  |  |  |
| Cosurfactant[5] | 0.5 |  |  |  |  | 2.0 |  |  | 2.0 | 2.0 | 2.0 | 2.0 |  | 2.0 | 2.0 | 2.0 |  |
| Cosurfactant[6] |  | 2.0 | 2.0 | 2.0 |  |  |  |  |  |  |  |  | 2.0 |  |  |  | 2.0 |
| Cosurfactant[7] |  |  |  |  | 2.0 |  |  | 2.0 |  |  |  |  |  |  |  |  |  |
| Cosurfactant[8] |  |  |  |  |  |  | 2.0 |  |  |  |  |  |  |  |  |  |  |
| Thickener[9] | 0.2 | 0.5 | 0.2 |  | 0.2 | 0.15 | 0.15 |  | 0.15 | 0.25 | 0.2 | 0.2 | 0.2 | 0.2 | 0.2 | 0.2 | 0.2 |
| Thickener[10] |  |  |  |  |  |  |  | 0.2 |  |  |  |  |  |  |  |  |  |
| Thickener[11] |  |  |  | 1.0 | 2.0 | 2.0 | 2.0 | 2.0 | 2.0 |  | 2.0 | 2.0 | 1.0 | 2.0 | 2.0 | 2.0 | 1.0 |
| Thickener[12] | 1.0 |  |  | 1.0 |  |  |  |  |  |  |  |  |  |  |  |  |  |
| Citric acid | 0.4 | 0.2 | 0.2 | 0.2 |  | 0.6 |  | 0.2 | 0.2 | 0.6 | 0.4 | 0.4 | 0.4 | 0.6 | 3.0 |  | 0.4 |
| KH$_2$PO$_4$ |  |  |  |  | 1.0 |  | 1.0 |  |  |  |  |  |  |  |  | 3.0 |  |
| Water to 100% |  |  |  |  |  |  |  |  |  |  |  |  |  |  |  |  |  |
| pH | 4.4 | 5.9 | 7.1 | 7.0 | 6.3 | 5.0 | 6.5 | 7.0 | 7.3 | 4.8 | 4.1 | 4.4 | 5.6 | 4.2 | 2.9 | 5.6 | 6.0 |

TABLE II

| Comparison Examples | 1 | 2 | 3 | 4 | 5 | 6 | 7 |
|---|---|---|---|---|---|---|---|
| Linuron | 17.3 | 17.3 | 17.3 | 17.3 | 17.3 | 17.3 | 17.3 |
| Monolinuron | 17.3 | 17.3 | 17.3 | 17.3 | 17.3 | 17.3 | 17.3 |
| Defoamer[1] | 2.0 | 2.0 | 2.0 | 2.0 | 2.0 | 2.0 |  |
| Defoamer[2] |  |  |  |  |  |  | 1.0 |
| Glycerol |  | 8.0 |  |  |  |  |  |
| Propylene glycol | 8.0 |  | 8.0 | 8.0 | 8.0 | 8.0 | 8.0 |
| Dispersant[3] |  | 4.0 | 5.0 | 4.0 | 4.0 |  |  |
| Dispersant[13] | 2.0 |  |  |  |  |  |  |
| Cosurfactant[6] | 2.0 | 2.0 |  | 2.0 |  | 2.0 | 2.0 |
| Cosurfactant[7] |  |  |  |  | 2.0 |  |  |
| Cosurfactant[5] |  |  | 2.0 |  |  |  |  |
| Thickener[9] |  |  | 0.15 | 0.25 |  |  | 0.2 |
| Thickener[10] |  |  |  |  | 0.2 |  |  |
| Thickener[11] | 1.0 | 1.0 | 2.0 | 1.0 | 2.0 | 1.0 | 1.0 |
| Thickener[12] | 1.0 | 1.0 |  |  |  | 1.0 |  |
| Citric acid | 0.2 |  |  |  |  | 0.2 |  |
| K citrate |  | 0.2 |  |  |  |  |  |
| KH$_2$PO$_4$ |  |  |  |  |  | 2.0 | 1.0 |
| Water to 100% |  |  |  |  |  |  |  |
| pH | 7.0 | 8.4 | 9.1 | >0.0 | 8.5 | 7.0 | 6.5 |

Notes to Tables I and II
[1] Defoamer based on silicone, commercial product SE 2 supplied by Wacker-Chemie GmbH;
[2] Defoamer based on silicone, commercial product Silicolapse ® 5020 supplied by Rhone Poulenc;
[3] Condensation product of 3 mol of nonylphenol and 2 mol of formaldehyde, oxethylated with 18 mol of ethylene oxide, reacted with 3 mol of maleic anhydride and 3 mol of sodium sulfite, in the form of a 35% strength aqueous solution;
[4] Commercial product Galoryl ® DT 12 supplied by CFPI, 92233 Gennevilliers, France; (sodium sulfonate of an aromatic polymer);
[5] Commercial product Galoryl ® DT201 supplied by CFPI; (condensed sulfonic acids in the form of the sodium salts);
[6] Commercial product Vanisperse ® CB supplied by Borregaard Industries Ltd., Sarpsborg, Norway; a lignosulfonate with 0.17 sulfonyl groups per phenylpropane unit, a total sulfur content of 2.4% and a pH of 8.8 (3% strength solution);
[7] Commercial product Vanisperse ®A supplied by Borregaard; a lignosulfonate with 0.17 sulfonyl groups per phenylpropane unit, a total sulfur content of 2.4% and a pH of 7.3 (3% strength solution);
[8] Commercial product Ligninsulfonat 300.36 ® (Lignosol FTA) supplied by Hansatronic;
[9] Commercial product Rhodopol ®23 supplied by Rhone Poulenc; a thickener based on polysaccharides;
[10] Commercial product Kelzan supplied by Kelco Corp., USA; a thickener based on polysaccharides;
[11] Thickener based on a mineral alumosilicate;
[12] Thickener based on colloidal Hg/Al silicate; commercial product Veegum ® supplied by Vanderbilt.
[13] Anionic condensation product based on cresols/formaldehyde/nonylphenol/sodium sulfite (HOES 1694)

I claim:

1. An aqueous herbicidal dispersion concentrate containing
   a) linuron and monolinuron as active substances, and
   b) an alkali metal salt of a sulfosuccinic monoester as dispersant, prepared by reacting a polyglycol ether of a condensation product of a (C$_8$ to C$_{12}$)-alkylphenol and formaldehyde with maleic anhydride, having a pH from 2.5 to 7.5.

2. The dispersion concentrate as claimed in claim 1, which contains furthermore
   (c) a cosurfactant selected from the group comprising lignosulfonates, alkali metal salts of a sulfonic acid of an aromatic condensation product, and alkali metal salts of a sulfonic acid of a polymeric aromatic substance.

3. The dispersion concentrate as claimed in claim 2, which contains 0.1 to 8% by weight, of component (c).

4. The dispersion concentrate as claimed in claim 1, in which the ratio by weight of linuron to monolinuron is 10:1 to 1:10.

5. The dispersion concentrate as claimed in claim 1, which contains linuron and monolinuron in each case in an amount of from approximately 8 to approximately 35% by weight.

6. The dispersion concentrate as claimed in claim 1, which contains 0.1 to 20% by weight, of component (b).

7. The dispersion concentrate as claimed in claim 1, which contains a buffer system based on citric acid and ammonium and/or alkaline earth metal salts thereof and dihydrogen phosphates as agents for adjusting the pH.

8. The dispersion concentrate as claimed in claim 1, which additionally contains thickeners, antifreeze agents, defoamers and/or preservatives.

9. The dispersion concentrate as claimed in claim 1, which has a pH of 3.5 to 7.0.

10. The dispersion concentrate as claimed in claim 1, which has a pH of 3.0.

11. The dispersion concentrate as claimed in claim 2, which contains 1 to 5% by weight, of component (c).

12. The dispersion concentrate as claimed in claim 1, in which the ratio by weight of linuron to monolinuron is approximately 1:1.

13. The dispersion concentrate as claimed in claim 1, which contains linuron and monolinuron in each case in an amount of from approximately 7 to 23% by weight.

14. The dispersion concentrate as claimed in claim 1, which contains 2 to 16% by weight, of component (b).

* * * * *